(12) United States Patent
Vath (10) Patent No.: US 9,839,622 B2
(45) Date of Patent: Dec. 12, 2017

(54) METHODS OF TREATING HYPOTHALAMIC OBESITY

(71) Applicant: Zafgen, Inc., Cambridge, MA (US)

(72) Inventor: James E. Vath, Lynnfield, MA (US)

(73) Assignee: Zafgen, Inc., Boston, MA (US)

( * ) Notice: Subject to any disclaimer, the term of this patent is extended or adjusted under 35 U.S.C. 154(b) by 0 days.

(21) Appl. No.: 14/399,391

(22) PCT Filed: May 8, 2013

(86) PCT No.: PCT/US2013/040077
§ 371 (c)(1),
(2) Date: Nov. 6, 2014

(87) PCT Pub. No.: WO2013/169857
PCT Pub. Date: Nov. 14, 2013

(65) Prior Publication Data
US 2015/0150840 A1    Jun. 4, 2015

Related U.S. Application Data

(60) Provisional application No. 61/644,051, filed on May 8, 2012.

(51) Int. Cl.
*A61K 31/336*    (2006.01)

(52) U.S. Cl.
CPC .................................. *A61K 31/336* (2013.01)

(58) Field of Classification Search
CPC ................................................... A61K 31/336
See application file for complete search history.

(56) References Cited

U.S. PATENT DOCUMENTS

| | | |
|---|---|---|
| 5,164,410 A | 11/1992 | Kishimoto et al. |
| 5,166,172 A | 11/1992 | Kishimoto et al. |
| 5,180,735 A | 1/1993 | Kishimoto et al. |
| 5,180,738 A | 1/1993 | Kishimoto et al. |
| 5,196,406 A | 3/1993 | Kamei et al. |
| 5,204,345 A | 4/1993 | Kishimoto et al. |
| 5,288,722 A | 2/1994 | Kishimoto et al. |
| 5,290,807 A | 3/1994 | Folkman et al. |
| 5,422,363 A | 6/1995 | Yanai et al. |
| 5,536,623 A | 7/1996 | Ohmachi et al. |
| 5,698,586 A | 12/1997 | Kishimoto et al. |
| 5,767,293 A | 6/1998 | Oku et al. |
| 5,846,562 A | 12/1998 | Yanai et al. |
| 5,900,431 A | 5/1999 | Molina et al. |
| 6,017,949 A | 1/2000 | D'Amato et al. |
| 6,017,954 A | 1/2000 | Folkman et al. |
| 6,040,337 A | 3/2000 | Hong, II et al. |
| 6,063,812 A | 5/2000 | Hong et al. |
| 6,180,626 B1 | 1/2001 | Shimomura et al. |
| 6,207,704 B1 | 3/2001 | Liu et al. |
| 6,242,494 B1 | 6/2001 | Craig et al. |
| 6,277,391 B1 | 8/2001 | Seo et al. |
| 6,306,819 B1 | 10/2001 | Rupnick et al. |
| 6,323,228 B1 | 11/2001 | BaMaung et al. |
| 6,383,471 B1 | 5/2002 | Chen et al. |
| 6,548,477 B1 | 4/2003 | Olson et al. |
| 6,566,541 B2 | 5/2003 | Liu et al. |
| 6,664,244 B1 | 12/2003 | Furuse et al. |
| 6,803,382 B2 | 10/2004 | Eustache et al. |
| 6,877,863 B2 | 4/2005 | Wood et al. |
| 6,989,392 B2 | 1/2006 | Collins et al. |
| 7,030,262 B2 | 4/2006 | BaMaung et al. |
| 7,037,890 B2 | 5/2006 | Olson et al. |
| 7,084,108 B2 | 8/2006 | Olson et al. |
| 7,268,111 B2 | 9/2007 | Olson et al. |
| 7,304,082 B2 | 12/2007 | Marino, Jr. et al. |
| 7,718,695 B2 | 5/2010 | Kim et al. |
| 8,367,721 B2 | 2/2013 | Hughes et al. |
| 8,642,650 B2 | 2/2014 | Hughes et al. |
| 8,980,946 B2 | 3/2015 | Hughes |
| 9,000,035 B2 | 4/2015 | Hughes |
| 9,173,865 B2 | 11/2015 | Hughes |
| 2003/0220371 A1 | 11/2003 | Kallander et al. |
| 2004/0067266 A1 | 4/2004 | Toppo |
| 2004/0116495 A1 | 6/2004 | Marino, Jr. et al. |
| 2004/0157836 A1 | 8/2004 | Comess et al. |
| 2004/0167128 A1 | 8/2004 | Comess et al. |
| 2004/0204472 A1 | 10/2004 | Briggs et al. |
| 2005/0037994 A1 | 2/2005 | Kim et al. |
| 2005/0239878 A1 | 10/2005 | Thompson et al. |
| 2006/0045865 A1 | 3/2006 | Jacob et al. |
| 2006/0069161 A1 | 3/2006 | Lee et al. |
| 2006/0276512 A1 | 12/2006 | Han et al. |
| 2007/0078172 A1 | 4/2007 | McElroy et al. |
| 2008/0200402 A1 | 8/2008 | Alvinerie et al. |
| 2009/0148396 A1 | 6/2009 | Akullian et al. |
| 2010/0016425 A1 | 1/2010 | Vath |
| 2010/0111894 A1 | 5/2010 | Benny-Ratsaby et al. |
| 2012/0004162 A1 | 1/2012 | Vath |
| 2012/0010259 A1 | 1/2012 | Vath |
| 2012/0010290 A1 | 1/2012 | Vath |
| 2012/0034233 A1 | 2/2012 | Hughes et al. |
| 2012/0322867 A1 | 12/2012 | Hughes et al. |
| 2013/0316994 A1 | 11/2013 | Hughes |
| 2014/0011870 A1 | 1/2014 | Hughes |
| 2014/0045934 A1 | 2/2014 | Hughes |
| 2014/0045935 A1 | 2/2014 | Hughes |
| 2014/0051752 A1 | 2/2014 | Hughes |
| 2014/0336251 A1 | 11/2014 | Hughes et al. |
| 2015/0209320 A1 | 7/2015 | Hughes et al. |
| 2015/0209321 A1 | 7/2015 | Hughes |
| 2015/0335608 A1 | 11/2015 | Hughes et al. |

FOREIGN PATENT DOCUMENTS

| | | |
|---|---|---|
| EP | 0682020 A1 | 11/1995 |
| WO | WO-98/56372 A1 | 12/1998 |

(Continued)

OTHER PUBLICATIONS

Kim, Y.M., et al. "Assessment of the anti-obesity effects of the TNP-470 analog, CKD-732." J. Molecular Endocrinology. (2007), vol. 38, pp. 455-465.*

(Continued)

*Primary Examiner* — Noble Jarrell
*Assistant Examiner* — John S Kenyon
(74) *Attorney, Agent, or Firm* — Goodwin Procter LLP (57) ABSTRACT

The invention generally relates to methods of treating a patient suffering from hypothalamic obesity using effective of amounts of a MetAP-2 inhibitor.

2 Claims, 3 Drawing Sheets

(56) References Cited

FOREIGN PATENT DOCUMENTS

| WO | WO-99/39702 A2 | 8/1999 |
|---|---|---|
| WO | WO-99/57097 A2 | 11/1999 |
| WO | WO-99/59986 A1 | 11/1999 |
| WO | WO-99/59987 A1 | 11/1999 |
| WO | WO-00/64876 A1 | 11/2000 |
| WO | WO-02/26782 A2 | 4/2002 |
| WO | WO-02/42295 A2 | 5/2002 |
| WO | WO-02/083065 A2 | 10/2002 |
| WO | WO-03/027104 A1 | 4/2003 |
| WO | WO-03/082845 A1 | 10/2003 |
| WO | WO-2004/033419 A1 | 4/2004 |
| WO | WO-2005/066197 A2 | 7/2005 |
| WO | WO-2005/082349 A1 | 9/2005 |
| WO | WO-2006/010498 A2 | 2/2006 |
| WO | WO-2006/080591 A1 | 8/2006 |
| WO | WO-2009/073445 A2 | 6/2009 |
| WO | WO-2010/042163 A2 | 4/2010 |
| WO | WO-2010/048499 A1 | 4/2010 |
| WO | WO-2010/065877 A2 | 6/2010 |
| WO | WO-2010/065879 A2 | 6/2010 |
| WO | WO-2010/065881 A2 | 6/2010 |
| WO | WO-2010/065883 A2 | 6/2010 |
| WO | WO-2011/044506 A2 | 4/2011 |
| WO | WO-2011/085198 A1 | 7/2011 |
| WO | WO-2011/085201 A1 | 7/2011 |
| WO | WO-2011/088055 A2 | 7/2011 |
| WO | WO-2011/127304 A2 | 10/2011 |
| WO | WO-2011/150338 A1 | 12/2011 |
| WO | WO-2012/012642 A1 | 1/2012 |
| WO | WO-2012/064838 A1 | 3/2012 |
| WO | WO-2012/051318 A1 | 4/2012 |
| WO | WO-2012/064928 A1 | 5/2012 |
| WO | WO-2012/074968 A1 | 6/2012 |
| WO | WO-2012/075020 A1 | 6/2012 |
| WO | WO-2012/075026 A1 | 6/2012 |
| WO | WO-2012/103333 A1 | 8/2012 |
| WO | WO-2012/122264 A1 | 9/2012 |
| WO | WO-2012/154676 A1 | 11/2012 |
| WO | WO-2012/154678 A1 | 11/2012 |
| WO | WO-2012/154679 A1 | 11/2012 |
| WO | WO-2013/033430 A1 | 3/2013 |
| WO | WO-2013/055385 A2 | 4/2013 |
| WO | WO-2013/109735 A1 | 7/2013 |
| WO | WO-2013/109739 A1 | 7/2013 |
| WO | WO-2013/169727 A1 | 11/2013 |
| WO | WO-2013/169860 A1 | 11/2013 |

OTHER PUBLICATIONS

The Free Dictionary. "Infiltrative." © 2016. Available from: < http://medical-dictionary.thefreedictionary.com/infiltrative >.*

Cleveland Clinic. "Acute Lymphocytic Leukemia (ALL)." (c) 2016. Available from: < http://my.clevelandclinic.org/health/diseases_conditions/hic_Leukemia/hic_Adult_Acute_Lymphoblastic_Leukemia >.*

Elfers, C., et al. "Robust Reductions of Excess Weight and Hyperphagia by Beloranib in Rat Models of Genetic and Hypothalamic Obesity." Endocrinology. (Jan. 2017), vol. 158, pp. 41-55.*

Anderson, "The Use of Fumagillin in Amoebiasis," Annals of the New York Academy of Sciences, 55:1118-1124, 1952.

Benny et al., "An Orally Delivered Small-Molecule Formulation with Antiangiogenic and Anticancer Activity," Nat Biotechnol. Jul. 2008;26(7):799-807.

Bernier et al.,"Fumagillin class inhibitors of methionine aminopeptidase-2," Drugs of the Future 30(5):497-500, 2005.

Brakenhielm et al., "Angiogenesis Inhibitor, TNP-470, Prevents Diet-Induced and Genetic Obesity in Mice" Circulation Research, http://circres.ahajournals.org (accessed on Feb. 8, 2007), 2004.

Braunwald et al., "Obesity" in Harrison's Principles of Internal Medicine, 15th Ed., McGraw Hill (New York) pp. 479-486, 2001.

Butler et al., "Clinical Findings and Natural History of Prader-Willi Syndrome," Chapter 1; Clinical Findings and Natural History of PWS, pp. 3-48 (2006).

Cassidy et al., "Prader-Willi syndrome," European Journal of Human Genetics 17:3-13 (2009).

Cassidy et al., "Prader-Willi syndrome," Genetics in Medicine, vol. 14(1) pp. 10-26 (2012).

Cataletto et al., "Prader-Willi syndrome: A primer for clinicians," International Journal of Pediatric Endocrinology, vol. 12:1-13 (2011).

Chun et al., "Novel inhibitors targeted to methionine aminopeptidase 2 (MetAP2) strongly inhibit the growth of cancers in xenografted nude model," Int J Cancer. Mar. 10, 2005;114(1):124-30.

Didier et al., "Antimicrosporidial Activities of Fumagillin, TNP-470, Ovalicin, and Ovalicin Derivatives in Vitro and In Vivo" Antimicrob Agents Chemother. Jun. 2006;50(6):2146-55.

DiPaolo et al.,"Studies on the Carcinolytic Activity of Fumagillin and Some of its Derivatives," Antibiot Annu.1958-1959;6:541-6.

Drevs et al.,"Antiangiogenic Potency of FK866/K22.175, a New Inhibitor of Intracellular NAD Biosynthesis, In Murine Renal Cell Carcinoma," Anticancer Res. Nov.-Dec. 2003;23(6C):4853-4858.

Dumas et al., "Synthesis and Structure Activity Relationships of Novel Small Molecule Cathepsin D Inhibitors" Bioorg Med Chem Lett. Sep. 6, 1999;9(17):2531-6.

Dykens et al., "Assessment of Hyperphagia in Prader-Willi Syndrome," Obesity 15:7 (2007).

Eder et al., "Phase 1 Dose Escalation Safety & Tolerance Study of PPI-2458 in Subjects with Non-Hodgkin's Lymphoma or Solid Tumors" (Presented on Nov. 7-10, 2006 at EORTC-NCI-AACR Symposium on "Molecular Targets and Cancer Therapeutics.").

Edgar et al., "Body composition in Prader-Willi syndrome compared with nonsyndromal obesity: Relationship to physical activity and growth homrone function," The Journal of Pediatrics 139:5, 708-714 (2001).

Einfield et al., "Mortality in Prader-Willi Syndrome," Am. J. Ment. Retard. 111(3):193-198 (2006).

European Communication for EP Application No. 12 798 444.1, dated Aug. 28, 2015 (8 pages).

European Search Report for EP 09798793 dated Oct. 11, 2011, 9 pages.

Evdokimov et al., "Serendipitious discovery of novel bacterial methionine aminopeptidase inhibitors," Proteins Feb. 15; 66(3):538-546 (2007).

Everhart, "Contributions of Obesity and Weight Loss to Gallstone Disease" Ann Intern Med. Nov. 15, 1993;119(10):1029-35.

Garrabrant et al.,"Small molecule inhibitors of methionine aminopeptidase type 2 (MetAP-2) fail to inhibit endothelial cell proliferation or formation of microvessels from rat aortic rings in vitro" Angiogenesis. 2004;7(2):91-6.

Garrison et al., "A metabolic basis for fibromyalgia and its related disorders: the possible role of resistance to thyroid hormone," Med. Hypotheses. Aug;61(2):182-189 (2003).

Han et al., "Design and Synthesis of Highly Potent Fumagillin Analogues from Homology Modeling for a Human MetAP-2," Bioorg Med Chem Lett. Jan. 3, 2000;10(1):39-43.

Holland et al., "The paradoc of Prader-Willi syndrome: a genetic model of starvation," The Lancet 362, 989-991 (2003).

Huang et al., "Inhibition of Monometalated Methionine Aminopeptidase: Inhibitor Discovery and Crystallographic Analysis," J. Med. Chem., Nov. 15;50(23):5735-5742 (2007).

Ingber et al., "Synthetic Analogues of Fumagillin that Inhibit Angiogenesis and Suppress Tumour Growth," Nature, 348(6301):555-557 (1990).

International Search Report for International Application No. PCT/US2011/020515, International Filing Date Jul. 1, 2011, 4 pages.

International Search Report for International Application No. PCT/US2011/020866, dated Jul. 22, 2011, 8 pages.

International Search Report for International Application No. PCT/US2011/060127, dated Jan. 2, 2012, 2 pages.

International Search Report for International Application No. PCT/US2011/062320, dated Feb. 17, 2012, 3 pages.

International Search Report for International Application No. PCT/US2011/062421, dated Feb. 17, 2012, 3 pages.

International Search Report for International Application No. PCT/US2011/38352, International Filing Date May 27, 2011,3 pages.

(56) References Cited

OTHER PUBLICATIONS

International Search Report for International Application No. PCT/US2012/000461, dated May 2, 2013, 7 pages.
International Search Report for International Application PCT/US2010/052050, dated Mar. 25, 2011, 3 pages.
Jauregi et al., "Behavioral profile of adults with Prader-Willi syndrome: correlations with individual and environmental variables," Journal of Neurodevelopmental Disorders 5:18, 1-10 (2013).
Jeong et al., "Total synthesis and antiangiogenic activity of cyclopentane analogues of fumagillol" Bioorg Med Chem Lett. Aug. 1;15(15):3580-3583 (2005).
Kawai et al., "Development of Sulfonamide Compounds as Potent Methionine Aminopeptidase Type II Inhibitors with Antiproliferative Properties", Bioorg. Med. Chem. Lett. Jul. 1;16(13):3574-3577 (2006).
Kim et al., "Assessment of the Anti-Obesity Effects of the TNP-470 Analog, CKD-732" J Mol Endocrinol. Apr;38(4):455-465 (2007).
Kim et al., "Development of parenteral formulation for a novel angiogenesis inhibitor, CKD-732 through complexation with hydroxypropyl-beta-cyclodextrin" Int J Pharm. Mar. 19;272(1-2):79-89 (2004).
Kim et al. "General pharmacology of CKD-732, a new anticancer agent: effects on central nervous, cardiovascular, and respiratory system" Biol Pharm Bull. Feb;28(2):217-223 (2005).
Kim et al., "Depletion of Methionine Aminopeptidase 2 does not Alter Cell Response to Fumagillin or Bengamides," Cancer Res., May 1;64(9):2984-2987 (2004).
Kruger, "TNP-470: An Angiogenesis Inhibitor in Clinical Development for Cancer" Expert Opin Investig Drugs. Jun;9(6):1383-1396 (2000).
Lee et al., "Absorption, distribution, metabolism, and excretion of CKD-732, a novel antiangiogenic fumagillin derivative, in rats, mice, and dogs" Arch Pharm Res. Feb;27(2):265-272 (2004).
Lee et al., "Design, Synthesis, and Antiangiogenic Effects of a Series of Potent Novel Fumagillin Analogues" Chem Pharm Bull (Tokyo). Jul;55(7):1024-1029 (2007).
Lee et al., "Selective N-demethylation of tertiary aminofumagillols with selenium dioxide via a non-classical Polonovski type reaction" Heterocycles 68(5):915-932 (2006).
Lijnen et al., "Fumagillin Reduces Adipose Tissue Formation in Murine Models of Nutritionally Induced Obesity" Obesity (Silver Spring).Dec;18(12):2241-2246 (2010).
Luo et al., "Discovery and Structural Modification of Inhibitors of Methionine Aminopeptidases from *Escherichia coli* and *Saccharomyces cerevisiae*," J. Med. Chem. Jun. 19;46(13):2631-2640 (2003).
Ma et al., "Structural Analysis of Inhibition of *E. coli* Methionine Aminopeptidase: Implication of Loop Adaptability in Selective Inhibition of Bacterial Enzymes," BMC Struct Biol., Dec. 19;7:84 (2007).
Masiero et al., "New Anti-angiogenesis Agents: Review of the Clinical Experience with Carboxyamido-Triazole (CAI), Thalidomide, TNP-470 and Interleukin-12" Angiogenesis;1(1):23-35 (1997).
McCowen et al., "Fumagillin (H-3), a New Antibiotic with Amebicidal Properties" Science. Feb. 23;113(2930):202-203 (1951).
Milkowski et al., "TNP-470" Antiangiogenic Agents in Cancer Therapy, Chapter 22 pp. 385-398, (1999).
Miller et al., "Nutritional Phases in Prader-Willi Syndrome," Am. J. Med. Genet. A. 155A(5): 1040-1049 (2011).
Molina et al., "Potential Efficacy of Fumagillin in Intestinal Microsporidiosis Due to Enterocytozoon Bieneusi in Patients with HIV Infection: Results of a Drug Screening Study" AIDS Nov;11(13):1603-1610 (1997).
Molina et al., "Fumagillin Treatment of Intestinal Microsporidiosis" N Engl J Med. Jun. 20;346(25):1963-1969 (2002).
Molina, et al., "Trial of Oral Fumagillin for the Treatment of Intestinal Microsporidiosis in Patients with HIV Infection" AIDS. Jul. 7;14(10):1341-1348 (2000).

Mosteller, R.D., "Simplified Calculation of Body-surface Area," N. Engl .J. Med., 317(17):1098 (Oct. 22, 1987).
Myung et al., "The identification of in vitro metabolites of CKD-732 by liquid chromatography/tandem mass spectrometry" Rapid Commun Mass Spectrom.;16(21):2048-2053 (2002).
Naganuma et al., "Metronomic doxifluridine chemotherapy combined with the anti-angiogenic agent TNP-470 inhibits the growth of human uterine carcinosarcoma xenografts" Cancer Sci. Aug;102(8):1545-52 (2011).
National Task Force on the Prevention and Treatment of Obesity "Very low-calorie diets. National Task Force on the Prevention and Treatment of Obesity, National Institutes of Health" JAMA, Aug. 25;270(8):967-974 (1993).
Noel et al. "Increased Risk of Acute Pancreatitis and Biliary Disease Observed in Patients with Type 2 Diabetes" Diabetes Care. May 2009;32(5):834-838 Feb. 2009.
Pagliarulo et al. "Gallstone disease and related risk factors in a large cohort of diabetic patients" Dig. Liver Dis., Feb;36(2):130-134 (2004).
Picoul et al., "Progress in fumagillin synthesis," Pure Appl. Chem. 75(2-3): 235-249 (2003).
Rhee et al., "Angiogenesis inhibitor attenuates parathyroid hormone-induced anabolic effect" Biomed Pharmacother. Jan;63(1):63-68 (2009).
Rupnick et al., "Adipose Tissue Mass Can be Regulated Through the Vasculature," Proc. Natl. Acad. Sci. U.S.A. Aug. 6;99(16):10730-10735 (2002).
Seneca et al., "Amebiasis: a review. II. Laboratory diagnosis, differential diagnosis and therapy," Am. J. Dig. Dis. Jul;1(7):310-322 (1956).
Sheppard et al., "3-Amino-2-Hydroxyamides and Related Compounds as Inhibitors of Methionine Aminopeptidase-2", Bioorg. Med. Chem Lett., Feb. 23;14(4):865-868 (2004).
Shin et al., "A Phase I Pharmacokinetic and Pharmacodynamic Study of CKD-732, an Antiangiogenic Agent, in Patients with Refractory Solid Cancer," Invest New Drugs Oct;28(5):650-658 (2010).
Shin et al., "A Phase lb pharmacokinetic study of the anti-angiogenic agent CKD-732 used in combination with capecitabine and oxaliplatin (XELOX) in metastatic colorectal cancer patients who progressed on irinotecan-based chemotherapy," Invest. New Drugs, Apr;30(2):672-680 (2012).
Srikumar et al., "Structural insights on Brugia malayi transglutaminase with cinnamoyl derivatives—a molecular docking approach," International Journal of Pharma and Bio Sciences 3(3):998-1006 (2012).
Towbin et al., "Proteomics-based target identification: bengamides as a new class of methionine aminopeptidase inhibitors," J. Biol. Chem. 278(52):52964-52971 (2003).
Vedantham et al., "Studies towards the synthesis of methionine aminopeptidase inhibitors: diversification utilizing a ROMP-derived coupling reagent", J Comb Chem. Mar.-Apr.;10(2):195-203 (2008).
Wang et al., "Lead optimization of methionine aminopeptidase-2 (MetAP2) inhibitors containing sulfonamides of 5,6-disubstituted anthranilic acids", Bioorg Med Chem Lett. May 15, 2007;17(10):2817-2822 (2007).
Wang et al., "Tumor Suppression by a Rationally Designed Reversible Inhibitor of Methionine Aminopeptidase-2", Cancer Res. 63:7861-7869 (2003).
Wang et al., "Discovery of inhibitors of *Escherichia coli* methionine aminopeptidase with the Fe(II)-form selectivity and antibacterial activity", J Med Chem. 51(19):6110-6120 (2008).
Weinsier et al., "Gallstone Formation and Weight Loss" Obes Res. Jan;1(1):51-56 (1993).
Weinsier et al., "Medically Safe Rate of Weight Loss for the Treatment of Obesity: A Guideline Based on Risk of Gallstone Formation" Am. J. Med. Feb;98(2):115-117 (1995).
Winter et al., "Endothelial anb3 Integrin-Targeted Fumagillin Nanoparticles Inhibit Angiogenesis in Atherosclerosis," Arterioscler Thromb Vasc. Biol., Sep;26(9):2103-2109 (2006).
Written Opinion for International Application No. PCT/US2009/066816, dated Apr. 8, 2010, 3 pages.

(56) References Cited

OTHER PUBLICATIONS

Written Opinion for International Application No. PCT/US2011/060127, dated May 10, 2013, 4 pages.
Written Opinion for International Application No. PCT/US2011/062320, dated May 29, 2013, 5 pages.
Yanai et al., "Antitumor Activity of a Medium-chain Triglyceride Solution of the Angiogenesis Inhibitor TNP-470 (AGM-1470) when Administered via the Hepatic Artery to Rats Bearing Walker 256 Carcinosarcoma in the Liver," J. Pharmacol. Exp. Ther. Dec;271(3):1267-1273 (1994).
Yanai et al., "Antitumor Effect of Arterial Administration of a Medium-Chain Triglyceride Solutionof an Angiogenesis Inhibitor, TNP-470, in Rabbits Bearing VX-2 Carcinoma," Pharm Res., May;12(5):653-657 (1995).
Zhang et al., "Angiogenesis Inhibitors Specific for Methionine Aminopeptidase 2 as Drugs for Malaria and Leishmaniasis," J. Biomed. Sci., 9(1):34-40 (Jan.-Feb. 2002).
U.S. Appl. No. 14/856,929, filed Sep. 17, 2015, Treatment of Obesity Using Non-Daily Administration of 6-O(4-Dimethylaminoethyoxy) Cinnamoyl Fumagillol.

* cited by examiner

METHODS OF TREATING HYPOTHALAMIC OBESITY

CROSS REFERENCE TO RELATED APPLICATIONS

This application claims priority to U.S. Provisional Ser. No. 61/644,051 filed May 8, 2012, hereby incorporated by reference in its entirety.

BACKGROUND

Hypothalamic obesity occurs subsequent to or in association with a pathological process injuring the hypothalamus. This syndrome is characterized by rapid, unrelenting weight gain that may be accompanied by severe hyperphagia. Weight gain of hypothalamic obesity is unlike that of normal obesity in that occurs even with caloric restriction. For example, following a hypothalamic lesion, patients develop a voracious hyperphagia that is hard to contain. Further, hypothalamic obesity is typically not responsive to diet and exercise.

Hypothalamic obesity can occur with any damage to or defect of the energy controlling centers of the hypothalamus. In particular, hypothalamic obesity is an unfortunate complication in some survivors of brain tumors, especially those diagnosed in childhood. It has been estimated that up to 75% of all survivors of craniopharyngioma develop severe obesity after diagnosis and treatment, with body weight rapidly accelerating after surgical resection of the tumor.

Hypothalamic obesity can also occur with genetic syndromes, such as in patients having mutations in leptin or leptin receptor, CART (cocaine and amphetamine-related transcript), POMC (proopiomelanocorgin), prophormone convertase, MC4R (melanocortin-4 receptor), singleminded 1 (a transcription factor essential for formation of the supraoptic and PVN nuclei in the hypothalamus), and TrkB. Prader-Willi syndrome, caused by deletion of paternally imprinted genes on chromosome 15q11-q13 and BBS (Bradet-Biedl syndrome) can also cause hypothalamic obesity. Further, many psychotropic drugs, for example, clozapine and olanzapine lead to hypothalamic-like obesity.

The hypothalamus regulates body weight by precisely balancing the intake of food, energy expenditure and amount of body fat tissue. The main hypothalamic areas involved in energy regulation (that when damaged cause hypothalamic obesity) include the ventromedial hypothalamus, paraventricular nuclei, arcuate nucleus and the lateral hypothalamic area. Further, signals from fat tissue mass in the body (including leptin) and from the gastrointestinal tract (including g GLP-1, PYY, and/or pancreatic insulin/amylin), affect the hypothalamic centers. Disorders involving any these type signals interaction with the hypothalamus, or damage to the hypothalamus, can lead to morbid, hypothalamic obesity. Weight gain occurs from the disruption of the normal homeostatic functioning of the hypothalamic centers, with loss of control of satiety and hunger, inability to regulate energy balance, reduction of energy expenditure, and/or hyperinsulinemia and frequent progression to diabetes. In contrast, "simple" obesity seems to result from patient variability in environmental cues, psychological/emotional status, and/or weight-regulating mechanisms.

Despite some understanding of the mechanism of hypothalamic obesity, treatment for hypothalamic obesity remains unsatisfactory and largely lacking, in part because there is an absence of well-established preventative or therapeutic strategies. Furthermore, hypothalamic obesity confers significant morbidity and mortality with a serious lack negative impact on those, for example, family members, who car for these patients.

SUMMARY

This disclosure generally relates to methods of treating hypothalamic obesity in an obese or overweight patient that includes administering an effective amount of a MetAP-2 inhibitor to a patient in need thereof. Also provided herein is a method of optimizing weight loss in a patient suffering from hypothalamic injury, comprising administering an amount of a MetAP-2 inhibitor to said patient.

For example, provided herein is a method of substantially maintaining body weight, or reducing the amount of weight gain in a patient recovering from, or initiating, craniopharyngioma surgical resection or radiological treatment of craniopharyngioma, comprising administering an effective amount of a MetAP-2 inhibitor Also provided herein is a method of treating, preventing, or ameliorating hypothalamic obesity in a patient being treated for schizophrenia or depression comprising administering an effective amount of a MetAP-2 inhibitor. Such patients being treated for schizophrenia or depression is or was administered amitriptyline, doxepin, imipramine, clomipramine, maprotiline, nortriptyline, trimipramine, paroxetine, mirtazapine, deopramine, isocarboxazid, lithium, valproate, carbamazapine, clozapine, olanzapine, zotepine, quetiapine, chlorpromazine, thioridazine, perphenazine, trifluoperazine, risperidone, clopenthioxol, or sulpiride.

Contemplated MetAP-2 inhibitors for use in the disclosed methods include substantially irreversible inhibitors, e.g., a MetAP-2 inhibitor is selected from the group consisting of a fumagillin, fumagillol or fumagillin ketone, siRNA, shRNA, an antibody, or a antisense compound, or O-(4-dimethylaminoethoxycinnamoyl)fumagillol and pharmaceutically acceptable salts thereof. Reversible inhibitors are also contemplated.

Human patients may have an initial body mass index of at least about 30 kg/m$^2$, at least about 35 kg/m$^2$, or at least 40 kg/m$^2$. Adolescent patients or children may have body mass index above the 95$^{th}$ percentile for children of the same age and sex, or a lower body mass index but clear cause for hypothalamic obesity that would benefit from earlier intervention. Also contemplated herein is a method of substantively preventing hypothalamic obesity in a patient suffering from hypothalamic injury, including administering a MetAP-2 inhibitor (e.g a disclosed MetAP-2 inhibitor), wherein the patient has a non-obesity body mass index (e.g., in the normal or overweight range), but is at risk of developing hypothalamic obesity.

Contemplated administration includes oral, subcutaneous administration and/or intravenous administration.

DETAILED DESCRIPTION

Methods

A method for treating hypothalamic obesity in a patient in need thereof, and/or a method for reducing body weight in a patient suffering from hypothalamic injury, is provided herein, comprising administering to the patient, on a daily or less than daily basis, a dose of a formulation comprising a therapeutically effective amount of a compound 6-O-(4-dimethylaminoethoxy)cinnamoyl fumagillol or pharmaceutically acceptable salts thereof. Such methods may include administering to the patient a single dose of the formulation about every other day (e.g., every two days), twice weekly (e.g. every 3 days, every 4 days, every 5 days, every 6 days or e.g. administered with an interval of about 2 to about 3 days between doses), once a week, every other week, twice monthly, once a month or even less often. It may be appreciated that methods that include administering a single dose on a less frequent basis, may, in some embodiments, be a method directed to maintaining a specific weight, such as a more optimal body weight after treatment using other methods disclosed herein. Disclosed methods may include e.g., administering a dose of a disclosed compound on a less than daily basis until a desired weight is achieved.

In some embodiments, disclosed methods relate to treating hypothalamic obesity that is result of hypothalamic injury due to infiltrative disease, tumor (e.g. such as a epithelioma, angiosarcoma, cholesteatoma, pinealoma, greminoma, endothelioma, hamartoma, chordoma, colloid cysts, epidermoid, ganglioneuroma, enpendymoma, glioma, meningioma, pituitary macroademona, teratoma, leukaemia, Langerhans cell, or metastatis tumor), neurosurgery, radiation, or head trauma. For example, provided herein is a method of treating, ameliorating and/or substantively preventing hypothalamic obesity that is a result of craniopharyngioma or following surgical or radiological treatment of craniopharyngioma in a patient.

Contemplated herein are methods of treating patient having hypothalamic obesity due to, (or treating patients at risk of having hypothalamic obesity due to) a disease such as sarcoidioisis, tuberculosis, arachniodits, histiocytosis X, or encephalitis. In other embodiments, methods of treating patients having hypothalamic obesity is contemplated, where the hypothalamic obesity is a result of cranial radiotherapy or cerebral aneurism, due to Prader-Willi syndrome or Bardet-Biedi syndrome, or due to a single or multiple gene mutation.

For example, provided herein is a method of substantially maintaining body weight, or reducing the amount of weight gain in a patient recovering from, or initiating, craniopharyngioma surgery or radiological treatment of craniopharyngioma, comprising administering an effective amount of a MetAP-2 inhibitor. Also provided herein is a method of substantially maintaining body weight, or minimizing weight gain in a patient suffering from Prader-Willi syndrome or Bardet-Biedi syndrome, comprising administering an effective amount of a MetAP-2 inhibitor.

Provided herein is a method of treating hypothalamic obesity in a patient being treated for schizophrenia or depression, and/or other associated mental disorders, and wherein the patient is or was administered a medication having as a side effect hypothalamic-like obesity (e.g., amitriptyline, doxepin, imipramine, clomipramine, maprotiline, nortriptyline, trimipramine, paroxetine, mirtazapine, deopramine, isocarboxazid, lithium, valproate, carbamazapine, clozapine, olanzapine, zotepine, quetiapine, chlorpromazine, thioridazine, perphenazine, trifluoperazine, risperidone, clopenthioxol, or sulpiride), comprising administering an effective amount of a disclosed MetAP-2 inhibitor.

Contemplated patients may be a human, (e.g. an adult, or a child under 18 years old), or a companion animal such as a cat or a dog.

A method for treating hypothalamic obesity in a patient in need thereof, and/or a method for reducing body weight, or minimizing or substantially preventing significant weight gain in a patient suffering from hypothalamic injury, is provided herein, comprising administering to the patient a dose of a formulation comprising a therapeutically effective amount of a compound 6-O-(4-dimethylaminoethoxy)cinnamoyl fumagillol or pharmaceutically acceptable salts thereof, for a first period of time, withheld for a second period of time, and again optionally administered for a third period of time, e.g., alternate dosing regimens. For example, for the first period of time a patient may be administered a disclosed formulation daily, every other day, every three, four or five days, biweekly, monthly, or yearly; during the second period of time (e.g. 1 day, 1 week, 2 weeks, 1 month) no dose is administered; and during e.g. a third period of time, the patient may be administered on a regimen similar or different to the first period of time, for example, every other day, every three, four or five days, biweekly, monthly, or yearly. At each administration or period time, the route of administration may be different or the same as another period of time.

The therapeutically effective amount administered in the disclosed methods such as those above may provide a patient with a body weight loss of about 0.3% to about 2%, about 0.4% to about 2%, or about 0.5% to about 2% or more, or about 0.5 kg to about 2 kg or more of the initial patient weight even after an initial dose, or after administration of two doses, or after administering after an first period of time, e.g., such methods may incur weight loss for three or four days or more after administration (e.g. parenteral (for example intravenous) administration) of a single dose. For example, a patient, after receiving a first dose and/or after receiving a subsequent dose, may continue to lose weight for three or four days or more without further administration of a disclosed compound. In some embodiments, administration of an initial first dose, or administration of a first and second dose (e.g., both administered in the same week), may provide about 0.5 kg to about 2 kg or more of weight loss. Subsequent administration may result in further weight loss, until a target patient weight is achieved.

In an embodiment, a method of ameliorating or preventing substantial weight gain in a patient having incurred a new hypothalamic injury, for example, by administering a disclosed MetAP2 inhibitor immediately or substantially immediately following such injury, for example, within 1 day, 1 week, 2 weeks, or within 3 weeks, or within one month or more post injury.

In another embodiment, provided herein are effective dosages, e.g. a daily dosage of a MetAP2 inhibitor, that may not substantially modulate or suppress angiogenesis. For example, provided here are methods that include administering doses of MetAP2 inhibitors that are effective for weight loss, but are significantly smaller doses than that necessary to modulate and/or suppress angiogenesis (which may typically require about 12.5 mg/kg to about 50 mg/kg or more). For example, contemplated dosage of a MetAP2 inhibitor in the methods described herein may include administering about 25 mg/day, about 10 mg/day, about 5 mg/day, about 3 mg/day, about 2 mg/day, about 1 mg/day, about 0.75 mg/day, about 0.5 mg/day, about 0.1 mg/day, about 0.05 mg/day, or about 0.01 mg/day.

For example, an effective amount of the drug for weight loss in a patient may be about 0.0001 mg/kg to about 25 mg/kg of body weight per day. For example, a contemplated dosage may from about 0.001 to 10 mg/kg of body weight (e.g. per day or every other day), about 0.001 mg/kg to 1 mg/kg of body weight, about 0.001 mg/kg to 0.1 mg/kg of body weight or about 0.005 to about 0.04 mg/kg or about 0.005 to about 0.049 mg/kg of body weight, about 0.01 to about 0.03 mg/kg of body weight, or about 0.005 to about 0.02 mg/kg. In an embodiment a MetAP2 inhibitor such as disclosed herein (e.g. O-(4-dimethlyaminoethoxycinnamoyl)fumagillol), may be administered about 0.005 to about 0.04 mg/kg of a patient, or another dosage amount as disclosed herein.

Contemplated doses, administered on a less than daily basis, may be a fixed dose, for example, about 0.3 mg, 0.5 mg, 1 mg, 2 mg, 1.5 mg, 1.8 mg, 2.5 mg, 3.0 mg, 4 mg, 5 mg or even 6 mg, e.g. about 0.5 mg to about 3.0 mg or about 0.1 mg to about 2 mg. In other embodiments, a therapeutically effective amount is based on excess body weight (or excess adipose tissue), for example, at least about 30 µg of a disclosed compound per kg of excess adipose tissue, (or excess body weight) of the patient, or least about 40 µg per kg or more of excess adipose tissue, (or excess body weight) of the patient, e.g., about 30 µg per kg of excess adipose tissue (or excess body weight) to about 60 µg per kg, about 40 µg per kg to about 60 µg per kg, or about 35 µg per kg to about 45 µg per kg, or about 35 µg per kg to about 50 µg per kg of excess adipose tissue (or excess body weight).

For example, provided herein is a method for treating obesity in a patient in need thereof, comprising administering, parenterally (e.g. intravenously) or non-parenterally (orallay), about 0.005 to about 0.04 mg/kg or about 0.01 to about 0.03 mg/kg, or about 0.01 to about 0.1 mg/kg of a MetAP2 inhibitor selected from O-(4-dimethylaminoethoxycinnamoyl)fumagillol and pharmaceutically acceptable salts thereof (for example, an oxalate salt), to said patient. Such a method, upon administration of said MetAP2 inhibitor e.g. daily or weekly, for about 3, 4, 5 or 6 months or more may result in at least a 10%, 20%, 30%, or 40% or more weight loss based on the patient's original weight.

Therapeutically effective doses may be calculated, for example, on the basis of body surface area (BSA), which can be determined using formulae such as those described by Mosteller (Mosteller R D, N Engl J Med 1987 Oct. 22; 317(17):1098), in which BSA is calculated in SI units as BSA $(m^2)=([Height (cm) \times Weight (kg)]/3600)^{1/2}$ (e.g. BSA=SQRT((cm*kg)/3600)), or US units, in which BSA $(m^2)=([Height(in) \times Weight (lbs)]/3131)^{1/2}$. In some embodiments, the therapeutically effective amount administered (e.g., intravenously) to patient using a disclosed method is about 0.5 mg/m$^2$ to about 1.5 mg/m$^2$, or about 0.9 mg/m$^2$ (or approximately 10 to 20 µg per kilo of total body weight) or more of a disclosed compound. In other embodiments, a therapeutically effective amount is based on excess body weight (or excess adipose tissue), for example, at least about 30 µg of a disclosed compound per kg of excess adipose tissue, (or excess body weight) of the patient, or least about 40 µg per kg or more of excess adipose tissue, (or excess body weight) of the patient, e.g., about 30 µg per kg of excess adipose tissue (or excess body weight) to about 60 µg per kg, about 40 µg per kg to about 60 µg per kg, or about 35 µg per kg to about 45 µg per kg, or about 35 µg per kg to about 50 µg per kg of excess adipose tissue (or excess body weight).

In another embodiment, a method of treating obesity in a patient in need thereof is provided, comprising administering an effective amount of a MetAP-2 inhibitor, wherein the effective amount is proportional to excess body weight of said patient. For example, in some embodiments, such effective amount may not be proportional to total body weight. A method of treating obesity in a patient in need thereof is also provided, comprising determining the excess body weight or excess adipose tissue of said patient; determining an effective dose of a MetAP-2 based on the excess body weight or adipose tissue for said patient; and administering the effective dose to said patient.

For example, disclosed methods may include administering (e.g. parenterally administering) to the patient a single dose of at least about 40 µg of 6-O-(4-dimethylaminoethoxy)cinnamoyl fumagillol or pharmaceutically acceptable salts thereof, per kg of excess adipose tissue of the patient, e.g. daily, less than daily, etc. In some embodiments, such methods may further include administering a second dose of at least about 40 µg of 6-O-(4-dimethylaminoethoxy)cinnamoyl fumagillol or pharmaceutically acceptable salts thereof, per kg of excess body weight of the patient at least about 4 days after administration of the single dose. A second dose, for example, may be administered at intervals of e.g., three or four days or more. In another embodiments, disclosed methods may further include administering subsequent doses of a MetAP2 inhibitor (e.g. —O-(4-dimethylaminoethoxy)cinnamoyl fumagillol) at intervals of between about 4 days and 1 month.

Also provided herein is a method of optimizing weight loss in a patient undergoing weight loss treatment and suffering from hypothalamic injury is provided, comprising a) administering an amount of a MetAP-2 inhibitor to said patient; b) determining the increase in adiponectin in said patient; and c) increasing the amount of the MetAP-2 inhibitor administered to the patient if the change in adiponectin in the patient is less than an increase of about 60% or more (or 50% or more, e.g. 30% to about 60% as compared to the adiponectin level of the patient before administration of the MetAP-2 inhibitor.

In another embodiment, a method of optimizing weight loss in a patient undergoing weight loss treatment and suffering from hypothalamic injury is provided, comprising a) administering an amount of a MetAP-2 inhibitor to said patient; b) determining the increase in adiponectin in said patient; c) increasing the amount of the MetAP-2 inhibitor administered to the patient if a reduction in the ratio of leptin to adiponectin in the plasma of the patient is not greater than 50%, or not greater than 40%, e.g., the reduction of the ratio of leptin to adiponection is reduced by about 10%, 20%, 30% or 40%.

In an embodiment, a method of treating or ameliorating hypothalamic obesity in a patient in need thereof, comprising administering a disclosed MetAP-2 inhibitor to patient in conjunction with bariatric surgery, e.g. before and/or after such surgery.

In addition to being hypothalamically overweight or obese, a patient may be suffering from other overweight- or obesity-related co-morbidities, i.e., diseases and other adverse health conditions associated with, exacerbated by, or precipitated by being overweight or obese. Because being overweight or obese is associated with other adverse health conditions or co-morbidities, for example diabetes, administering MetAP2 inhibitors may bring a benefit in ameliorating, arresting development of or, in some cases, even eliminating, these overweight- or obesity-related conditions or co-morbidities. In some embodiments, disclosed methods include co-administration with hormones such as growth hormones that may be required in patients with hypothalamic injury. In some embodiments, methods provided herein may further include administering at least one other agent in addition to a MetAP2 inhibitor, e.g., an agent directed to treatment of these overweight- or obesity-related conditions.

Contemplated other agents include those administered to treat type 2 diabetes such as sulfonylureas (e.g., chlorpropamide, glipizide, glyburide, glimepiride); meglitinides (e.g., repaglinide and nateglinide); biguanides (e.g., metformin); thiazolidinediones (rosiglitazone, troglitazone, and pioglitazone); glucagon-like 1 peptide mimetics (e.g. exenatide and liraglutide); sodium-glucose cotransporter inhibitors (e.g., dapagliflozin), renin inhibitors, and alpha-glucosidase inhibitors (e.g., acarbose and meglitol), and/or those administered to treat cardiac disorders and conditions, such hypertension, dyslipidemia, ischemic heart disease, cardiomyopathy, cardiac infarction, stroke, venous thromboembolic disease and pulmonary hypertension, which have been linked to overweight or obesity, for example, chlorthalidone; hydrochlorothiazide; indapamide, metolazone; loop diuretics (e.g., bumetanide, ethacrynic acid, furosemide, lasix, torsemide); potassium-sparing agents (e.g., amiloride hydrochloride, spironolactone, and triamterene); peripheral agents (e.g., reserpine); central alpha-agonists (e.g., clonidine hydrochloride, guanabenz acetate, guanfacine hydrochloride, and methyldopa); alpha-blockers (e.g., doxazosin mesylate, prazosin hydrochloride, and terazosin hydrochloride); beta-blockers (e.g., acebutolol, atenolol, betaxolol, nisoprolol fumarate, carteolol hydrochloride, metoprolol tartrate, metoprolol succinate, Nadolol, penbutolol sulfate, pindolol, propranolol hydrochloride, and timolol maleate); combined alpha- and beta-blockers (e.g., carvedilol and labetalol hydrochloride); direct vasodilators (e.g., hydralazine hydrochloride and minoxidil); calcium antagonists (e.g., diltiazem hydrochloride and verapamil hydrochloride); dihydropyridines (e.g., amlodipine besylate, felodipine, isradipine, nicardipine, nifedipine, and nisoldipine); ACE inhibitors (benazepril hydrochloride, captopril, enalapril maleate, fosinopril sodium, lisinopril, moexipril, quinapril hydrochloride, ramipril, trandolapril); angiotensin II receptor blockers (e.g., losartan potassium, valsartan, and Irbesartan); and combinations thereof, as well as statins such as mevastatin, lovastatin, pravastatin, simvastatin, velostatin, dihydrocompactin, fluvastatin, atorvastatin, dalvastatin, carvastatin, crilvastatin, bevastatin, cefvastatin, rosuvastatin, pitavastatin, and glenvastatin, typically for treatment of dyslipidemia.

Other agents that may be co-administered (e.g. sequentially or simultaneously) include agents administered to treat ischemic heart disease including statins, nitrates (e.g., Isosorbide Dinitrate and Isosorbide Mononitrate), beta-blockers, and calcium channel antagonists, agents administered to treat cardiomyopathy including inotropic agents (e.g., Digoxin), diuretics (e.g., Furosemide), ACE inhibitors, calcium antagonists, anti-arrhythmic agents (e.g., Sotolol, Amiodarone and Disopyramide), and beta-blockers, agents administered to treat cardiac infarction including ACE inhibitors, Angiotensin II receptor blockers, direct vasodilators, beta blockers, anti-arrhythmic agents and thrombolytic agents (e.g., Alteplase, Retaplase, Tenecteplase, Anistreplase, and Urokinase), agents administered to treat strokes including anti-platelet agents (e.g., Aspirin, Clopidogrel, Dipyridamole, and Ticlopidine), anticoagulant agents (e.g., Heparin), and thrombolytic agents, agents administered to treat venous thromboembolic disease including anti-platelet agents, anticoagulant agents, and thrombolytic agents, agents administered to treat pulmonary hypertension include inotropic agents, anticoagulant agents, diuretics, potassium (e.g., K-dur), vasodilators (e.g., Nifedipine and Diltiazem), Bosentan, Epoprostenol, and Sildenafil, agents administered to treat asthma include bronchodilators, anti-inflammatory agents, leukotriene blockers, and anti-Ige agents. Particular asthma agents include Zafirlukast, Flunisolide, Triamcinolone, Beclomethasone, Terbutaline, Fluticasone, Formoterol, Beclomethasone, Salmeterol, Theophylline, and Xopenex, agents administered to treat sleep apnea include Modafinil and amphetamines, agents administered to treat nonalcoholic fatty liver disease include antioxidants (e.g., Vitamins E and C), insulin sensitizers (Metformin, Pioglitazone, Rosiglitazone, and Betaine), hepatoprotectants, and lipid-lowering agents, agents administered to treat osteoarthritis of weight-bearing joints include Acetaminophen, non-steroidal anti-inflammatory agents (e.g., Ibuprofen, Etodolac, Oxaprozin, Naproxen, Diclofenac, and Nabumetone), COX-2 inhibitors (e.g., Celecoxib), steroids, supplements (e.g. glucosamine and chondroitin sulfate), and artificial joint fluid, agents administered to treat Prader-Willi Syndrome include human growth hormone (HGH), somatropin, and weight loss agents (e.g., Orlistat, Sibutramine, Methamphetamine, Ionamin, Phentermine, Bupropion, Diethylpropion, Phendimetrazine, Benzphetermine, and Topamax), agents administered to treat polycystic ovary syndrome include insulin-sensitizers, combinations of synthetic estrogen and progesterone, Spironolactone, Eflornithine, and Clomiphene, agents administered to treat erectile dysfunction include phosphodiesterase inhibitors (e.g., Tadalafil, Sildenafil citrate, and Vardenafil), prostaglandin E analogs (e.g., Alprostadil), alkaloids (e.g., Yohimbine), and testosterone, agents administered to treat infertility include Clomiphene, Clomiphene citrate, Bromocriptine, Gonadotropin-releasing Hormone (GnRH), GnRH agonist, GnRH antagonist, Tamoxifen/nolvadex, gonadotropins, Human Chorionic Gonadotropin (HCG), Human Menopausal Gonadotropin (HmG), progesterone, recombinant follicle stimulating hormone (FSH), Urofollitropin, Heparin, Follitropin alfa, and Follitropin beta, agents administered to treat obstetric complications include Bupivacaine hydrochloride, Dinoprostone PGE2, Meperidine HCl, Ferro-folic-500/iberet-folic-500, Meperidine, Methylergonovine maleate, Ropivacaine HCl, Nalbuphine HCl, Oxymorphone HCl, Oxytocin, Dinoprostone, Ritodrine, Scopolamine hydrobromide, Sufentanil citrate, and Oxytocic, agents administered to treat depression include serotonin reuptake inhibitors (e.g., Fluoxetine, Escitalopram, Citalopram, Paroxetine, Sertraline, and Venlafaxine); tricyclic antidepressants (e.g., Amitriptyline, Amoxapine, Clomipramine, Desipramine, Dosulepin hydrochloride, Doxepin, Imipramine, Iprindole, Lofepramine, Nortriptyline, Opipramol, Protriptyline, and Trimipramine); monoamine oxidase inhibitors (e.g., Isocarboxazid, Moclobemide, Phenelzine, Tranylcypromine, Selegiline, Rasagiline, Nialamide, Iproniazid, Iproclozide, Toloxatone, Linezolid, Dienolide kavapyrone desmethoxyyangonin, and Dextroamphetamine); psychostimulants (e.g., Amphetamine, Methamphetamine, Methylphenidate, and Arecoline); antipsychotics (e.g., Butyrophenones, Phenothiazines, Thioxanthenes, Clozapine, Olanzapine, Risperidone, Quetiapine, Ziprasidone, Amisulpride, Paliperidone, Symbyax, Tetrabenazine, and Cannabidiol); and mood stabilizers (e.g., Lithium carbonate, Valproic acid, Divalproex sodium, Sodium valproate, Lamotrigine, Carbamazepine, Gabapentin, Oxcarbazepine, and Topiramate), agents administered to treat anxiety include serotonin reuptake inhibitors, mood stabilizers, benzodiazepines (e.g., Alprazolam, Clonazepam, Diazepam, and Lorazepam), tricyclic antidepressants, monoamine oxidase inhibitors, and beta-blockers, and other weight loss agents, including serotonin and noradrenergic re-uptake inhibitors; noradrenergic re-uptake inhibitors; selective serotonin re-uptake inhibitors; and intestinal lipase inhibitors. Particular weight loss agents include orlistat, sibutramine, methamphetamine, ionamin, phentermine, bupropion, diethylpropion, phendimetrazine, benzphetermine, and topamax.

Contemplated modes of administration of Met-AP2 inhibitors in the disclosed methods include subcutaneous, intravenous or oral administration. For example, injectable preparations are contemplated herein, for example, sterile injectable aqueous or oleaginous suspensions may be formulated according to the known art using suitable dispersing or wetting agents and suspending agents.

Disclosed or contemplated treatment regimens can include a corrective phase, during which a MetAP2 inhibitor dose sufficient to provide reduction of excess adiposity is administered e.g. initially upon hypothalamic injury (e.g., following surgery), followed by a maintenance phase, during which a lower or equivalent MetAP2 inhibitor dose sufficient to prevent re-development of excess adiposity may be administered.

Obesity and being overweight refer to an excess of fat in proportion to lean body mass. Excess fat accumulation is associated with increase in size (hypertrophy) as well as number (hyperplasia) of adipose tissue cells. Obesity is variously measured in terms of absolute weight, weight:height ratio, degree of excess body fat, distribution of subcutaneous and/or visceral fat, and societal and esthetic norms. A common measure of body fat is Body Mass Index (BMI). The BMI refers to the ratio of body weight (expressed in kilograms) to the square of height (expressed in meters). Body mass index may be accurately calculated using the formulas: SI units: BMI=weight (kg)/(height$^2$ (m$^2$), or US units: BMI=(weight(b)*703)/(height$^2$ (in$^2$).

In accordance with the U.S. Centers for Disease Control and Prevention (CDC), an overweight adult has a BMI of 25 kg/m$^2$ to 29.9 kg/m$^2$, and an obese adult has a BMI of 30 kg/m$^2$ or greater. A BMI of 40 kg/m$^2$ or greater is indicative of morbid obesity or extreme obesity. For children, the definitions of overweight and obese take into account age, stature, and gender as they relate to what are appropriate amounts of body fat and do not strictly rely on upon BMI calculations. It may be appreciated that for certain patients (e.g., certain ethnic groups, e.g. Asian), a lower BMI may be consideration overweight or obese.

BMI does not account for the fact that excess adipose can occur selectively in different parts of the body, and development of adipose tissue can be more dangerous to health in some parts of the body rather than in other parts of the body. For example, "central obesity", typically associated with an "apple-shaped" body, results from excess adiposity especially in the abdominal region, including belly fat and intra-abdominal or visceral fat, and carries higher risk of co-morbidity than "peripheral obesity", which is typically associated with a "pear-shaped" body resulting from excess adiposity especially on the hips. Measurement of waist/hip circumference ratio (WHR) can be used as an indicator of central obesity. A minimum WHR indicative of central obesity has been variously set, and a centrally obese adult typically has a WHR of about 0.85 or greater if female and about 0.9 or greater if male. Methods of determining whether a subject is overweight or obese that account for the ratio of excess adipose tissue to lean body mass may involve obtaining a body composition of the subject. Body composition can be obtained by measuring the thickness of subcutaneous fat in multiple places on the body, such as the abdominal area, the subscapular region, arms, buttocks and thighs. These measurements are then used to estimate total body fat with a margin of error of approximately four percentage points. Another method is bioelectrical impedance analysis (BIA), which uses the resistance of electrical flow through the body to estimate body fat. Another method is using a large tank of water to measure body buoyancy. Increased body fat will result in greater buoyancy, while greater muscle mass will result in a tendency to sink. Yet another method is fan-beam dual energy X-ray absorptiometry (DEXA). DEXA allows body composition, particularly total body fat and/or regional fat mass, to be determined non-invasively.

Excess body weight may be assessed, for example, by comparing the weight of a patient in need of treatment to the weight of the same patient that would achieve a desired, e.g. non-obese, BMI (e.g. a desired BMI of about 25 or less). For example, excess body weight of a 1.6 m in height patient weighing 89.6 kg (and having a BMI of 35) may be found by calculating the weight required for a BMI of 25 (i.e., about 64 kg); the initial excess body weight of such patient would about 89.6−64=25.6 kg.

MetAP2 Inhibitors

MetAP2 inhibitors refer to a class of molecules that inhibit or modulate the activity of MetAP2, e.g., the ability of MetAP2 to cleave the N-terminal methionine residue of newly synthesized proteins to produce the active form of the protein, or the ability of MetAP2 to regulate protein synthesis by protecting the subunit of eukaryotic initiation factor-2 (eIF2) from phosphorylation.

Exemplary MetAP2 inhibitors may include irreversible inhibitors that covalently bind to MetAP2. For example, such irreversible inhibitors include fumagillin, fumagillol, and fumagillin ketone.

Derivatives and analogs of fumagillin, and pharmaceutically acceptable salts thereof are contemplated herein as irreversible MetAP2 inhibitors, such as O-(4-dimethylaminoethoxycinnamoyl)fumagillol (also referred to herein as Compound A), O-(3,4,5-trimethoxycinnamoyl)fumagillol, O-(4-chlorocinnamoyl)fumagillol; O-(4-aminocinnamoyl)fumagillol; O-(4-dimethylaminoethoxycinnamoyl)fumagillol; O-(4-methoxycinnamoyl)fumagillol; O-(4-dimethylaminocinnamoyl)fumagillol; O-(4-hydroxycinnamoyl)fumagillol; O-(3,4-dimethoxycinnamoyl)fumagillol; O-(3,4-methylenedioxycinnamoyl)fumagillol; O-(3,4,5-trimethoxycinnamoyl)fumagillol; O-(4-nitrocinnamoyl)fumagillol; O-(3,4-dimethoxy-6-aminocinnamoyl)fumagillol; O-(4-acetoxy-3,5-dimethoxycinnamoyl)fumagillol; O-(4-ethylaminocinnamoyl)fumagillol; O-(4-ethylaminoethoxycinnamoyl)fumagillol; O-(3-dimethylaminomethyl-4-methoxycinnamoyl)fumagillol; O-(4-trifluoromethylcinnamoyl)fumagillol; O-(3,4-dimethoxy-6-nitrocinnamoyl)fumagillol; O-(4-acetoxycinnamoyl)fumagillol; O-(4-cyanocinnamoyl)fumagillol; 4-(4-methoxycinnamoyl)oxy-2-(1,2-epoxy-1,5-dimethyl-4-hexenyl)-3-methoxy-1-chloromethyl-1-cyclohexanol; O-(3,4,5-trimethoxycinnamoyl)fumagillol; O-(4-dimethylaminocinnamoyl)fumagillol; O-(3,4,5- trimethoxycinnamoyl)oxy-2-(1,2-epoxy-1,5-dimethyl-4-hexenyl)-3-methoxy-1-chloromethyl-1-cyclohexanol; O-(4-dimethylaminocinnamoyl)oxy-2-(1,2-epoxy-1,5-dimethyl-4-hexenyl)-3-methoxy-1-chloromethyl-1-cyclohexanol; O-(3,5-dimethoxy-4-hydroxycinnamoyl)fumagillol or O-(chloracetyl-carbamoyl) fumagillol (TNP-470), and/or pharmaceutically acceptable salts thereof (e.g. O-(4-dimethylaminoethoxycinnamoyl)fumagillol oxalate).

Fumagillin, and some derivatives thereof, have a carboxylic acid moiety and can be administered in the form of the free acid. Alternatively, contemplated herein are pharmaceutically acceptable salts of fumagillin, fumagillol, and derivatives thereof.

Pharmaceutically acceptable salts illustratively include those that can be made using the following bases: ammonia, L-arginine, benethamine, benzathene, betaine, bismuth, calcium hydroxide, choline, deanol, diethanolamine, diethylamine, 2-(diethylamino)ethanol, ethylenediamine, N-methylglucamine, hydrabamine, 1H-imidazole, lysine, magnesium hydroxide, 4-(2-hydroxyethyl)morpholine, piperazine, potassium hydroxide, 1-(2-hydroxyethyl)pyrrolidine, sodium hydroxide, triethanolamine, zinc hydroxide, diclyclohexlamine, or any other electron pair donor (as described in Handbook of Pharmaceutical Salts, Stan & Wermuth, VHCA and Wiley, Uchsenfurt-Hohestadt Germany, 2002). Contemplated pharmaceutically acceptable salts may include hydrochloric acid, bromic acid, sulfuric acid, phosphoric acid, nitric acid, formic acid, acetic acid, trifluoroacetic acid, oxalic acid, fumaric acid, tartaric acid, maleic acid, methanesulfonic acid, benzenesulfonic acid or para-toluenesulfonic acid.

Esters of the present invention may be prepared by reacting e.g. fumagillin or fumagillol with the appropriate acid under standard esterification conditions described in the literature (Houben-Weyl 4th Ed. 1952, Methods of Organic Synthesis). Suitable fumagillin esters include ethyl methanoate, ethyl ethanoate, ethyl propanoate, propyl methanoate, propyl ethanoate, and methyl butanoate.

In another embodiment, contemplated irreversible inhibitors of MetAP2 may include a siRNA, shRNA, an antibody or an antisense compound of MetAP2.

Further examples of reversible and irreversible MetAP2 inhibitors are provided in the following references, each of which is hereby incorporated by reference: Olson et al. (U.S. Pat. No. 7,084,108 and WO 2002/042295), Olson et al. (U.S. Pat. No. 6,548,477; U.S. Pat. No. 7,037,890; U.S. Pat. No. 7,084,108; U.S. Pat. No. 7,268,111; and WO 2002/042295), Olson et al. (WO 2005/066197), Hong et al. (U.S. Pat. No. 6,040,337), Hong et al. (U.S. Pat. No. 6,063,812 and WO 1999/059986), Lee et al. (WO 2006/080591), Kishimoto et al. (U.S. Pat. No. 5,166,172; U.S. Pat. No. 5,698,586; U.S. Pat. No. 5,164,410; and 5,180,738), Kishimoto et al. (U.S. Pat. No. 5,180,735), Kishimoto et al. (U.S. Pat. No. 5,288,722), Kishimoto et al. (U.S. Pat. No. 5,204,345), Kishimoto et al. (U.S. Pat. No. 5,422,363), Liu et al. (U.S. Pat. No. 6,207,704; U.S. Pat. No. 6,566,541; and WO 1998/056372), Craig et al. (WO 1999/057097), Craig et al. (U.S. Pat. No. 6,242,494), BaMaung et al. (U.S. Pat. No. 7,030,262), Comess et al. (WO 2004/033419), Comess et al. (US 2004/0157836), Comess et al. (US 2004/0167128), Henkin et al. (WO 2002/083065), Craig et al. (U.S. Pat. No. 6,887,863), Craig et al. (US 2002/0002152), Sheppard et al. (2004, Bioorganic & Medicinal Chemistry Letters 14:865-868), Wang et al. (2003, Cancer Research 63:7861-7869), Wang et al. (2007, Bioorganic & Medicinal Chemistry Letters 17:2817-2822), Kawai et al. (2006, Bioorganic & Medicinal Chemistry Letters 16:3574-3577), Henkin et al. (WO 2002/026782), Nan et al. (US 2005/0113420), Luo et al. (2003, J. Med. Chem., 46:2632-2640), Vedantham et al. (2008, J. Comb. Chem., 10:195-203), Wang et al. (2008, J. Med. Chem., 51 (19):6110-20), Ma et al. (2007, BMC Structural Biology, 7:84) and Huang et al. (2007, J. Med. Chem., 50:5735-5742), Evdokimov et al. (2007, PROTEINS: Structure, Function, and Bioinformatics, 66:538-546), Garrabrant et al. (2004, Angiogenesis 7:91-96), Kim et al. (2004, Cancer Research, 64:2984-2987), Towbin et al. (2003, The Journal of Biological Chemistry, 278(52):52964-52971), Marino Jr. (U.S. Pat. No. 7,304,082), Kallender et al. (U.S. patent application number 2004/0192914), and Kallender et al. (U.S. patent application numbers 2003/0220371 and 2005/0004116). Other MetAP2 inhibitors contemplated herein are disclosed in U.S. Ser. No. 61/310,776; 61/293,318; 61/366,650 and PCT/US10/52050 (all of the above are hereby incorporated by reference in their entirety).

For example, contemplated MetAP2 inhibitors may include:

EXAMPLES

The examples which follow are intended in no way to limit the scope of this invention but are provided to illustrate aspects of the disclosed methods. Many other embodiments of this invention will be apparent to one skilled in the art.

Example 1: Mouse Model of Hypothalamic Injury

Gold thioglucose (GTG) is a chemical treatment used as a model of hypothalamic injury. C57/BL6 mice were treated with single dose of 0.5 g/kg gold thioglucose. After 40 days a cohort was started on 0.1 mg/kg daily subcutaneous dose of 6-O-(4-dimethylaminoethoxy)cinnamoyl fumagillol (ZGN-440).

Figure 1:
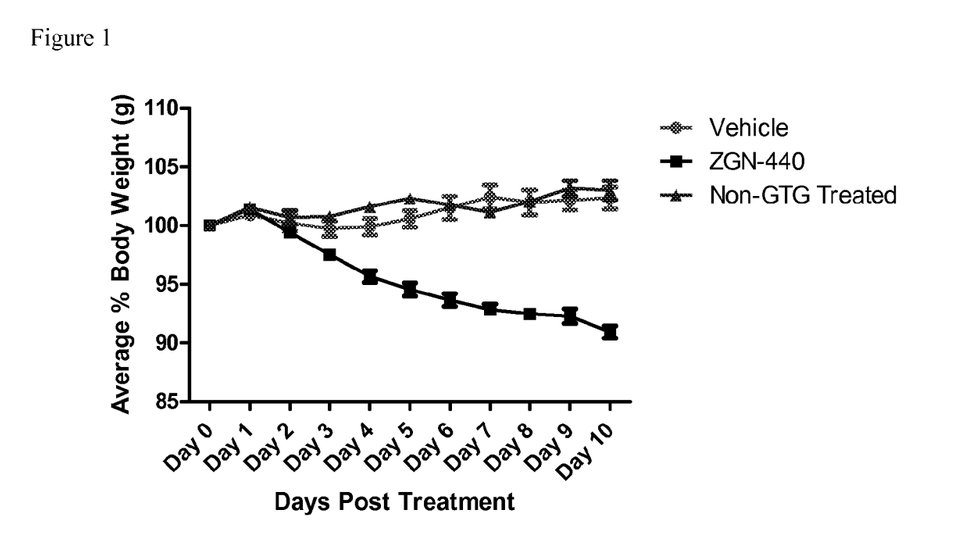
FIG. 1 depicts body weight change (percent) of C57/BL6 mice treated with single dose of 0.5 g/kg gold thioglucose, and after 40 days, started on 0.1 mg/kg daily subcutaneous dose of 6-O-(4-dimethylaminoethoxy)cinnamoyl fumagillol (ZGN-440).
Figure 2:
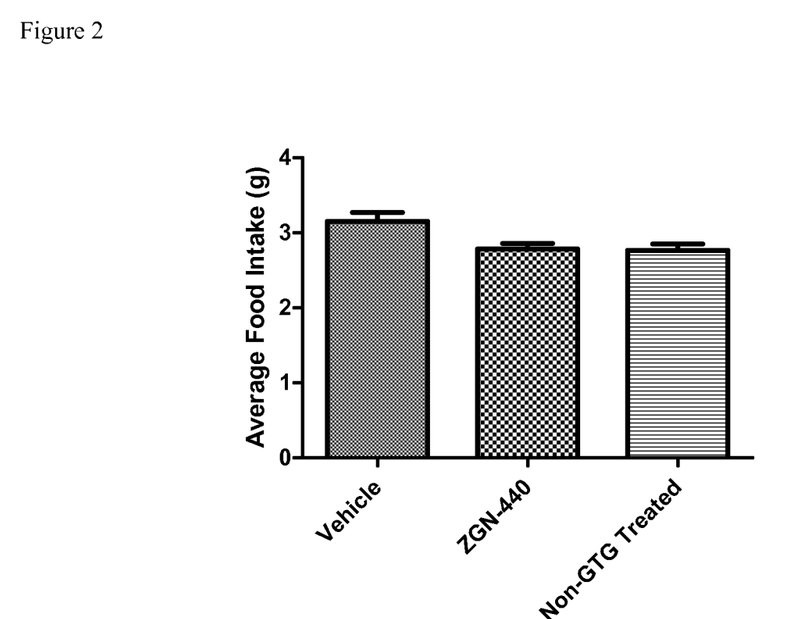
FIG. 2 depicts normalized food intake in GTG mice to the level of normal mice that were not treated with gold thioglucose, after 0.1 mg/kg daily subcutaneous dose of 6-O-(4-dimethylaminoethoxy)cinnamoyl fumagillol.

Significant weight loss was observed in the treated mice approximating the weight loss we have seen in other obesity models. (FIG. 1). The food intake level of GTG treated mice was increased to over 3 g/day/mouse, where in GTG mice treated with ZGN-440 the food intake decreased to the level of normal mice that were not treated with gold thioglucose (below 3 g/day). (FIG. 2).

Figure 3:
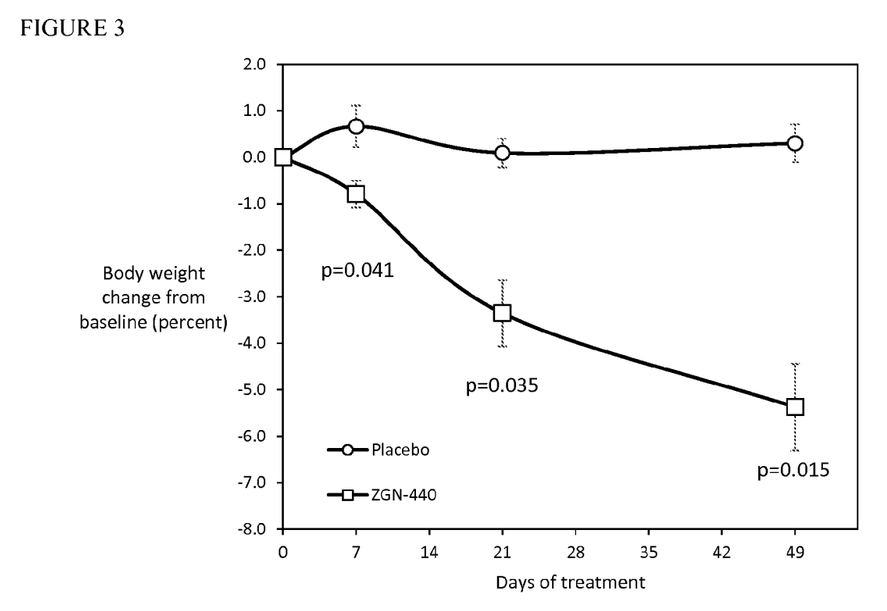
FIG. 3 depicts percentage reduction in body weight by up to seven weeks of treatment with 6-O-(4-dimethylaminoethoxy)cinnamoyl fumagillol (ZGN-440; average dose of 1.44 mg administered twice weekly by subcutaneous administration, n=5) or placebo (administered twice weekly by subcutaneous administration, n=2) in obese human patients treated otherwise for depression with mirtazapine, sertraline, imipramine, paroxetine, or amitryptyline.

Example 2: Effects of Treatment of Humans Otherwise Treated with Anti-Depressants Known to Cause Hypothalamic Obesity Significant weight loss was observed over a period of up to seven weeks of treatment of obese humans also taking anti-depressant medications (e.g., mirtazapine, sertraline, imipramine, paroxetine, and amitriptyline) known to induce body weight gain and obesity. Five of these patients were also administered ZGN-440 (average dose of 1.44 mg, administered twice weekly by subcutaneous administration). On average, patients lost 5.4 percent of their baseline body weight over the seven week treatment. In contrast, similar patients (also taking anti-depressant medications known to induce body weight gain and obesity, including mirtazapine, sertraline, imipramine, paroxetine, and amitryptyline) treated with placebo, administered twice weekly by subcutaneous administration, failed to lose weight. At baseline, the average (±SEM) body weight was 100.2±3.2 kg, and the average body mass index was 38.8±1.7 kg/m$^2$. Weight loss was statistically significant for ZGN-440 vs. placebo as indicated (p values derived using the Student's t test for percent change of body weight from baseline). (FIG. 3).

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method of treating hypothalamic obesity in a patient suffering from Prader-Willi syndrome, comprising parenterally administering 2 or 3 times a week a pharmaceutically effective amount of 6-O-(4-dimethylaminoethoxycinnamoyl)fumagillol or a pharmaceutically acceptable salt thereof to said patient.

2. The method of claim 1, wherein parenterally administering is subcutaneously administering.

* * * * *